US00PP35160P2

(12) United States Plant Patent
Moon

(10) Patent No.: US PP35,160 P2
(45) Date of Patent: May 9, 2023

(54) ***QUERCUS* 'QPMTF2'**

(50) Latin Name: *Quercus phellos*
Varietal Denomination: QPMTF2

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/903,690

(22) Filed: Sep. 6, 2022

(51) Int. Cl.
*A01H 5/00* (2018.01)

(52) U.S. Cl.
USPC ..... Plt./225

(58) Field of Classification Search
USPC ..... Plt./225
See application file for complete search history.

*Primary Examiner* — Annette H Para
(74) *Attorney, Agent, or Firm* — Cassandra Bright

(57) ABSTRACT

A new and distinct cultivar of *Quercus phellos* tree named 'QPMTF2' is disclosed, characterized by distinctive small, dark green foliage. The canopy of the tree is dense and broadly pyramidal. Foliage is held on the tree long into Fall. The new variety is a *Quercus* tree, typically used for landscapes and gardens.

3 Drawing Sheets

Latin name of the genus and species: *Quercus phellos.*
Variety denomination: 'QPMTF2'.

BACKGROUND OF THE INVENTION

The new cultivar is a product of a planned breeding program. The new variety was discovered growing as a seedling among a group of open-pollinated *Quercus phellos* trees at a tree farm in Washington, Ga. The inventor made this discovery in 2009. The exact seed and pollen parents cannot be identified.

Asexual reproduction by grafting of the new cultivar 'QPMTF2' was first performed during summer of 2010 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Quercus phellos* tree as particularly evidenced by the smaller leaf, darker more dense willow oak, holds foliage longer, dark green mature growth against bright new growth, and dominant central leader. These genetic traits can be consistently reproduced by asexual propagation.

SUMMARY OF THE INVENTION

The cultivar 'QPMTF2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QPMTF2' grown in Washington, Ga. These characteristics in combination distinguish 'QPMTF2' as a new and distinct *Quercus phellos* cultivar:

1. Small foliage.
2. Dark green foliage.
3. Holds foliage longer into the Fall than commercially known varieties.
4. Dark green mature growth against bright new growth.
5. Dominant central leader.
6. Dense canopy.

PARENT COMPARISON

The parent varieties cannot be specifically identified.

COMMERCIAL COMPARISON

Plants of the new cultivar 'QPMTF2' are similar to plants of *Quercus phellos* 'QPSTJ', U.S. Plant Pat. No. 19,922, in most horticultural characteristics, however, plants of the new cultivar 'QPMTF2' differ in the following:

1. The new variety has a broader canopy than this comparator.
2. The new variety holds its leaves longer into Fall than this comparator.

Plants of the new cultivar 'QPMTF2' are similar to plants of *Quercus phellos* 'QPSTA', U.S. Plant Pat. No. 13,677, in most horticultural characteristics, however, plants of the new cultivar 'QPMTF2' differ in the following:

1. The new variety has smaller foliage than this comparator.
2. The new variety holds its leaves longer into Fall than this comparator.

Plants of the new cultivar 'QPMTF2' are similar to plants of *Quercus phellos* 'QPSTB', U.S. Plant Pat. No. 18,321, in most horticultural characteristics, however, plants of the new cultivar 'QPMTF2' differ in the following:

1. The new variety has a broader canopy than this comparator.
2. The new variety holds its leaves longer into Fall than this comparator.
3. The new variety has yellow Fall foliage; this comparator has red Fall foliage.

Plants of the new cultivar 'QPMTF2' are similar to plants of *Quercus phellos* 'RT3', U.S. Plant Pat. No. 16,444, in most horticultural characteristics, however, plants of the new cultivar 'QPMTF2' differ in the following:

1. The new variety has a broader canopy than this comparator.
2. The new variety holds its leaves longer into Fall than this comparator.

Plants of the new cultivar 'QPMTF2' are similar to plants of *Quercus phellos* 'QPMTF', U.S. Plant Pat. No. 15,217, in most horticultural characteristics, however, plants of the new cultivar 'QPMTF2' differ in the following:

1. The new variety has smaller foliage than this comparator.
2. The new variety holds its leaves longer into Fall than this comparator.

BRIEF DESCRIPTION OF THE PHOTOGRAPHS

The accompanying photograph in FIG. 1 illustrates a tree of the new variety at about 7 years of age.

Figure 1:
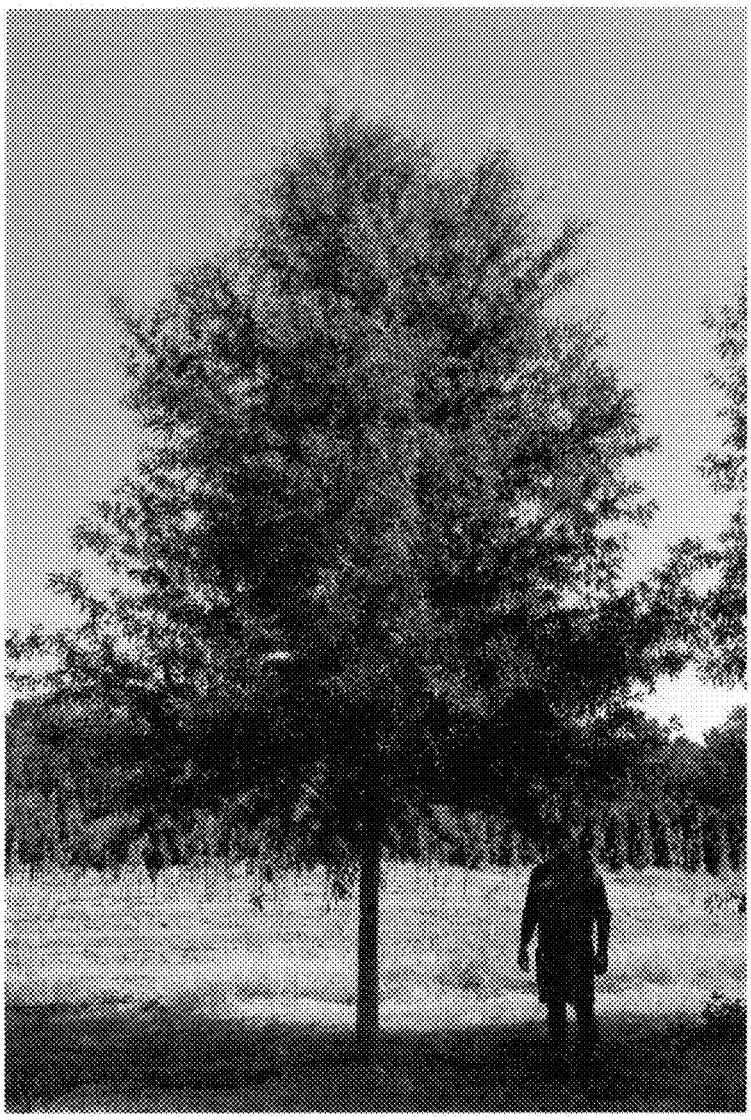
Figure 2:
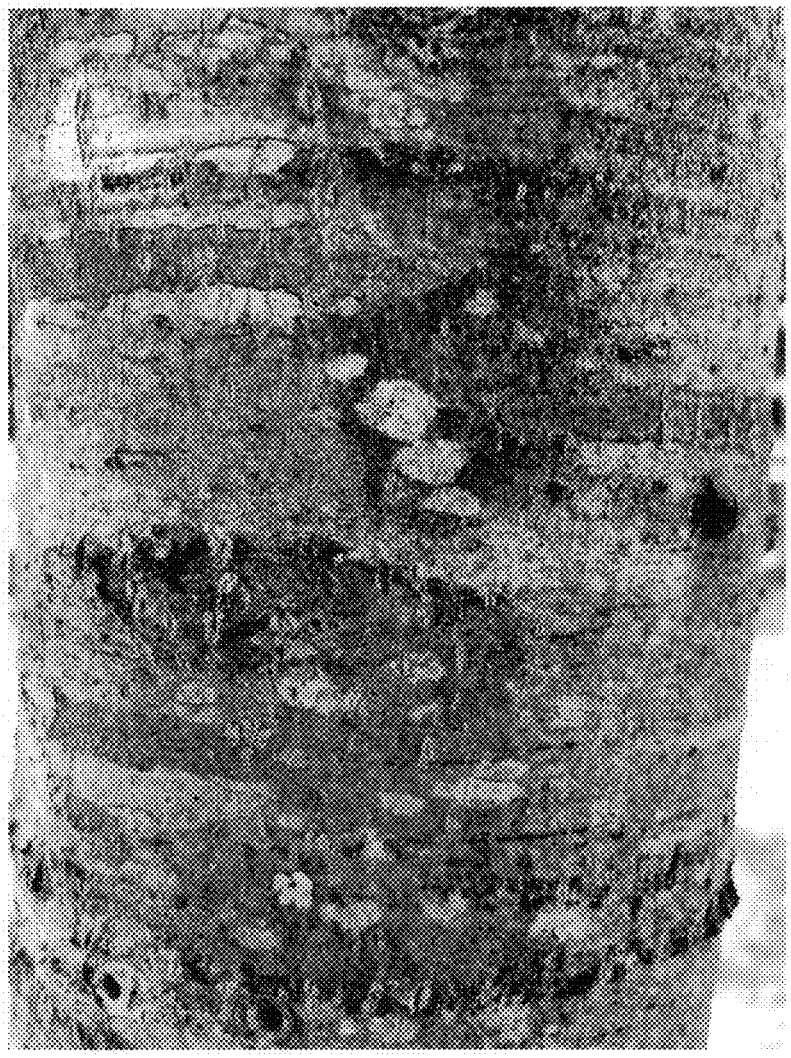
FIG. 2 illustrates a close-up view of the trunk surface.
Figure 3:
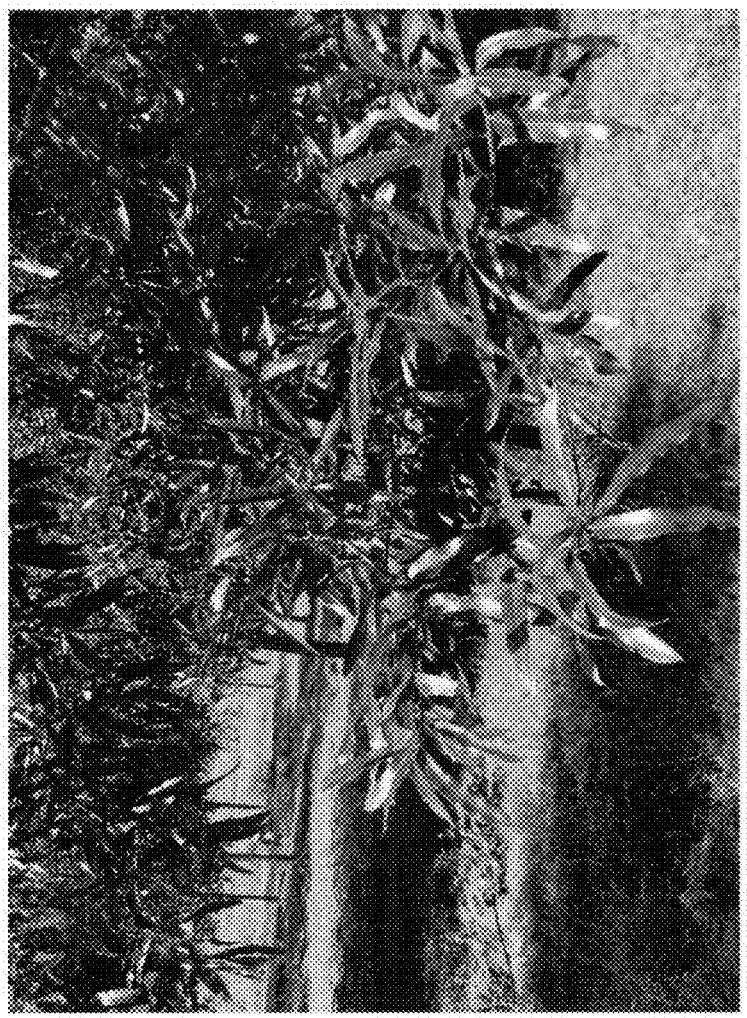
FIG. 3 illustrates a view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'QPMTF2' plants grown outdoors and in a nursery in Washington, Ga. Plants are approximately 2 years old, in a 3 gallon nursery container. Temperatures ranged from 5° C. to 10° C. at night to 18° C. to 27° C. during the day. Measurements and numerical values represent averages of typical plant types.

Botanical classification: *Quercus phellos* 'QPMTF2'.

PROPAGATION

Cleft grafting.

Root description: Woody. Brown roots not accurately measured with an R.H.S. Colour chart.

TREE

Growth habit: Deciduous broad pyramidal tree.

Height: Approximately 14 feet at 3 years.

Spread: Approximately 4 feet at 3 years.

Aspect and angle: Branches at 45 degrees or more from center.

Growth rate: Rapid.

Trunk characteristics:

*Diameter*.—About 3 inches measured at approximately 3 inches above soil level at 3 years.

*Color*.—Near RHS Greyed-Green 198A, 198C with blotches Black 202A.

*Surface texture*.—Furrowed and scaly.

FOLIAGE

Leaf:

*Arrangement*.—Alternate.

*Shape*.—Lanceolate or narrow elliptic.

*Average length*.—Average 7.5 cm to 8.5 cm excluding petiole.

*Average width*.—Approximately 1 cm.

*Apex*.—Acute.

*Base*.—Tapered.

*Margin*.—Entire

*Texture of top surface*.—Glabrous.

*Texture of lower surface*.—Glabrous.

*Color*.—Young foliage: Upper side: Near RHS Green 143A. Under side: Near RHS Green 143B. Mature foliage: Upper side: Near RHS Green 139A. Under side: Near RHS Green 137A.

*Venation*.—Type: Pinnate. Color: Venation color upper side: Near RHS Yellow-Green 144C. Venation color under side: Near RHS Yellow-Green N144A.

*Petiole*.—Length: Average 1 cm. Diameter: Average 2 mm. Color: Upper side: Near RHS Yellow-Green 144A. Under side: Near RHS Yellow-Green 144C.

FLOWER

Not observed.

REPRODUCTIVE ORGANS

Not observed.

OTHER CHARACTERISTICS

Disease/pest resistance: Neither resistance nor susceptibility to normal diseases and pests of *Quercus* has been observed.

Drought tolerance: No tolerance for drought observed. *Quercus phellos* can be moderately drought tolerance once established.

Temperature tolerance: USDA Zones 6 through 9.

Fruits/nuts: Not observed.

What is claimed is:

1. A new and distinct cultivar of *Quercus phellos* tree named 'QPMTF2' as herein illustrated and described.

* * * * *